(12) United States Patent
Bronson

(10) Patent No.: US 6,546,559 B1
(45) Date of Patent: Apr. 15, 2003

(54) AUXILIARY VISOR FOR RIDER'S HELMET

(76) Inventor: Kim M. Bronson, 3210 Retreat Ct., Malibu, CA (US) 90265

( * ) Notice: Subject to any disclaimer, the term of this patent is extended or adjusted under 35 U.S.C. 154(b) by 0 days.

(21) Appl. No.: 10/068,743

(22) Filed: Feb. 11, 2002

(51) Int. Cl.[7] .................................................. A61F 9/00
(52) U.S. Cl. .................. 2/12; 2/10; 2/209.12; 2/175.6; 2/209.3
(58) Field of Search ........................ 2/10, 12, 209.13, 2/209.12, 175.6, 209.3

(56) References Cited

U.S. PATENT DOCUMENTS

| | | | | |
|---|---|---|---|---|
| 317,972 A | * | 5/1885 | Cary ........................ | 2/175.6 |
| 514,278 A | * | 2/1894 | Roedel, Jr. ................ | 2/175.6 |
| 642,440 A | * | 1/1900 | Gerstle ..................... | 2/10 |
| 770,352 A | * | 9/1904 | Cleveland ................. | 2/10 |
| 3,613,115 A | * | 10/1971 | Hill .......................... | 2/10 |
| 4,896,375 A | * | 1/1990 | Colucci ..................... | 2/12 |
| 4,993,081 A | * | 2/1991 | Fulghum ................... | 2/209.12 |
| 5,406,645 A | * | 4/1995 | Lin .......................... | 2/10 |
| 5,862,520 A | * | 1/1999 | Wyant ...................... | 2/10 |
| 6,081,922 A | * | 7/2000 | Wright ..................... | 2/12 |

FOREIGN PATENT DOCUMENTS

EP          498562 A1 * 8/1992 ............ A42B/1/06

* cited by examiner

*Primary Examiner*—Rodney M. Lindsey
(74) *Attorney, Agent, or Firm*—Elliott N. Kramsky

(57) ABSTRACT

An auxiliary visor for a standard riding helmet. The visor includes a bill fixed to an elongated flexible band. Facing sides of the ends of the band include mating fasteners that permit the band to surround and apply an inwardly-directed force to the exterior surface of a helmet. The interior surface of the band includes a strip of material of predetermined non-sticky composition.

5 Claims, 3 Drawing Sheets

AUXILIARY VISOR FOR RIDER'S HELMET

BACKGROUND

1. Field of the Invention

The present invention relates to gear for use in horseback riding. More particularly, this invention pertains to an auxiliary visor for a rider's helmet.

2. Description of the Prior Art

Outdoor activities such as horseback riding subjects one to considerable exposure to the sun. For this reason, protective riding helmets commonly include a brim or bill to shade the rider's face.

Riding helmets come in standard sizes and configurations. Unfortunately, many standard riding helmets possess bills of insufficient size to shade the rider's face effectively. As a result, the rider is often subject to undesirable amounts of ultraviolet radiation. This may lead to undesired "leathering" of the skin as well as skin cancers and melanomas.

SUMMARY OF THE INVENTION

The present invention addresses the foregoing shortcomings of the prior art by providing an auxililary visor adaptable to a riding helmet. Such visor includes a bill for shading a wearer. Such visor includes at least one edge.

A band is fixed to such edge of the bill. Such band comprises an elongated member of flexible material having interior and exterior surfaces and opposed ends. A fastener is provided for securing the band to surround and apply an inwardly-directed force to the exterior surface of a helmet. Such fastener comprises mating cooperative elements fixed in facing relationship to the opposed ends of the member.

The interior surface comprises a strip of material that includes a material of predetermined non-sticky composition for imposing, in combination with the inwardly-directed force, a frictional force for retaining the band to a riding helmet.

The preceding and other features and advantages of this invention will become further apparent from the detailed discussion that follows. Such description is accompanied by a set of drawing figures. Numerals of the drawing figures, corresponding to those of the written description, point to the features of the invention with like numerals referring to like features throughout.

DETAILED DESCRIPTION OF THE PREFERRED EMBODIMENT

Figure 1:
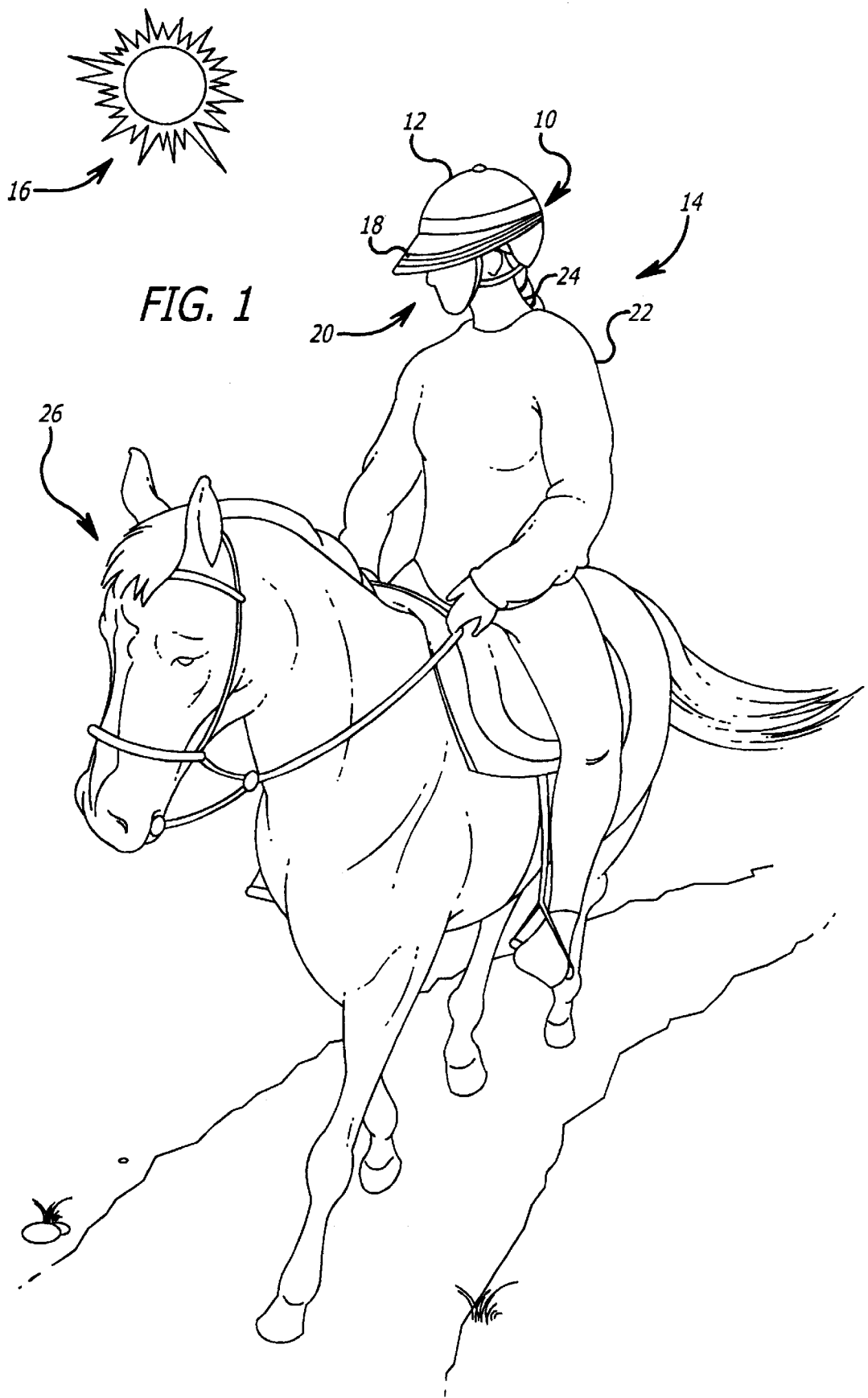
FIG. 1 is a perspective view of an auxiliary visor for a helmet in accordance with the invention in use.

FIG. 1 is a perspective view of an auxiliary visor 10 mounted for use with a rider's helmet 12 in accordance with the invention. Such an auxiliary visor 10 provides essential additional protection for a wearer 14 against the often-harmful rays of the sun 16. The conventional riding helmet 12 comes in a number of standard sizes and features a forward-looking bill 18 (shown in shadow outline) that offers often-insufficient protection of the wearer's face 20 and little, if any protection from the sun for the wearer's back 22 and neck 24. The auxiliary visor 10 of the invention blocks the rays of the sun 16 from the skin of these easily-damaged areas.

The auxiliary visor 10 must be physically compatible in all respects, including size and weight with the helmet 12 while overcoming the above-stated shortcomings of the forward-looking bill 18. In addition, it must be securely adherent to riding helmets 12 of differing surface finishes, both glossy and matte. In addition, the auxiliary visor 10 must be resistant to unintended decoupling from the helmet 12 during foreseeable conditions of use, including rushing wind and the g-forces occasioned by the up-and-down trotting movement of a horse 26.

Figure 2:
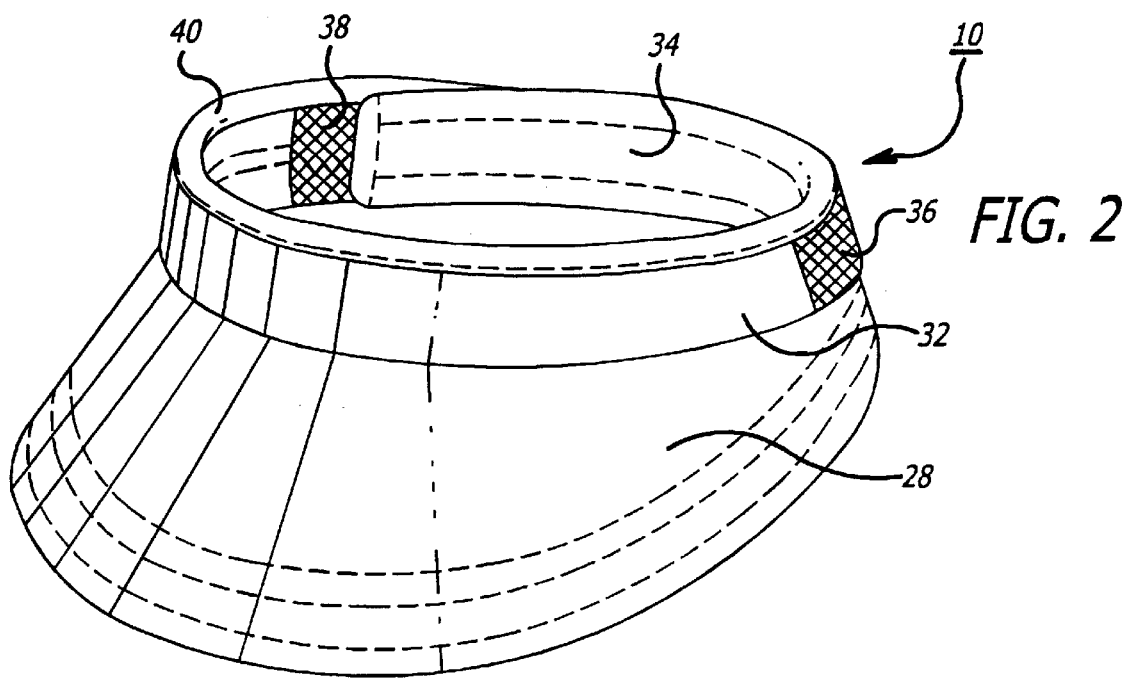
FIG. 2 is a perspective view of the visor of the invention.
Figure 3:
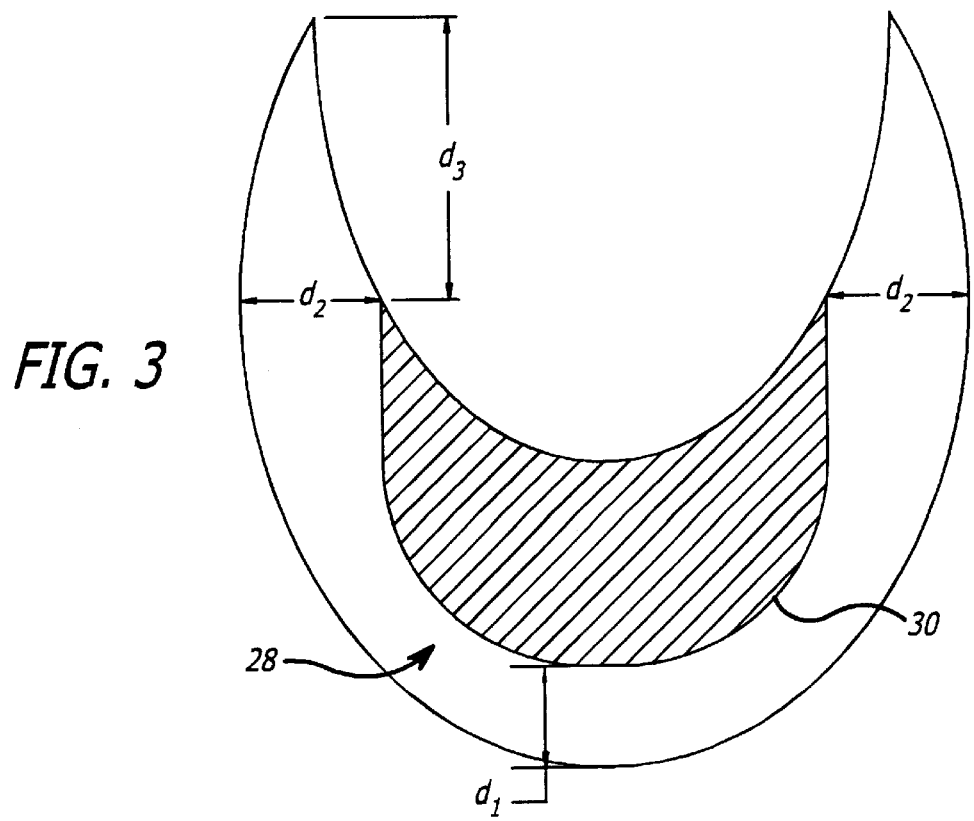
FIG. 3 is a top plan view of the bill of the auxiliary visor of the invention overlying that of a conventional riding helmet (in shading) for illustrating the relative sizes thereof.

FIG. 2 is a perspective view of the visor 10 of the invention. The visor 10 includes an oversized bill 28 that provides shading and peripheral visibility well beyond that of that of a conventional riding helmet. This may be readily in FIG. 3, a top plan view of the bill 28 overlying the shaded outline 30 of a conventional riding helmet. As can be seen, the bill 28 extends beyond the front of the bill of the conventional riding helmet by an amount $d_1$ and provides lateral coverage of up to $d_2$ that extends $d_3$ to the rear of any shading offered by a conventional helmet.

Returning to FIG. 2, the bill 28 is preferably formed of plastic board overcovered with fabric. The plastic board, as opposed to cardboard, provides additional resilience and stiffness for repeated use. It is joined to a front panel 32 that, in turn, is sewn to a back panel 34. The front panel 32 includes a strip 36 of VELCRO hook material for mating with a strip 38 of VELCRO loop material that is fixed to the back panel 34. A top binding 40 joins the front and back panels 32 and 34.

Figure 4:
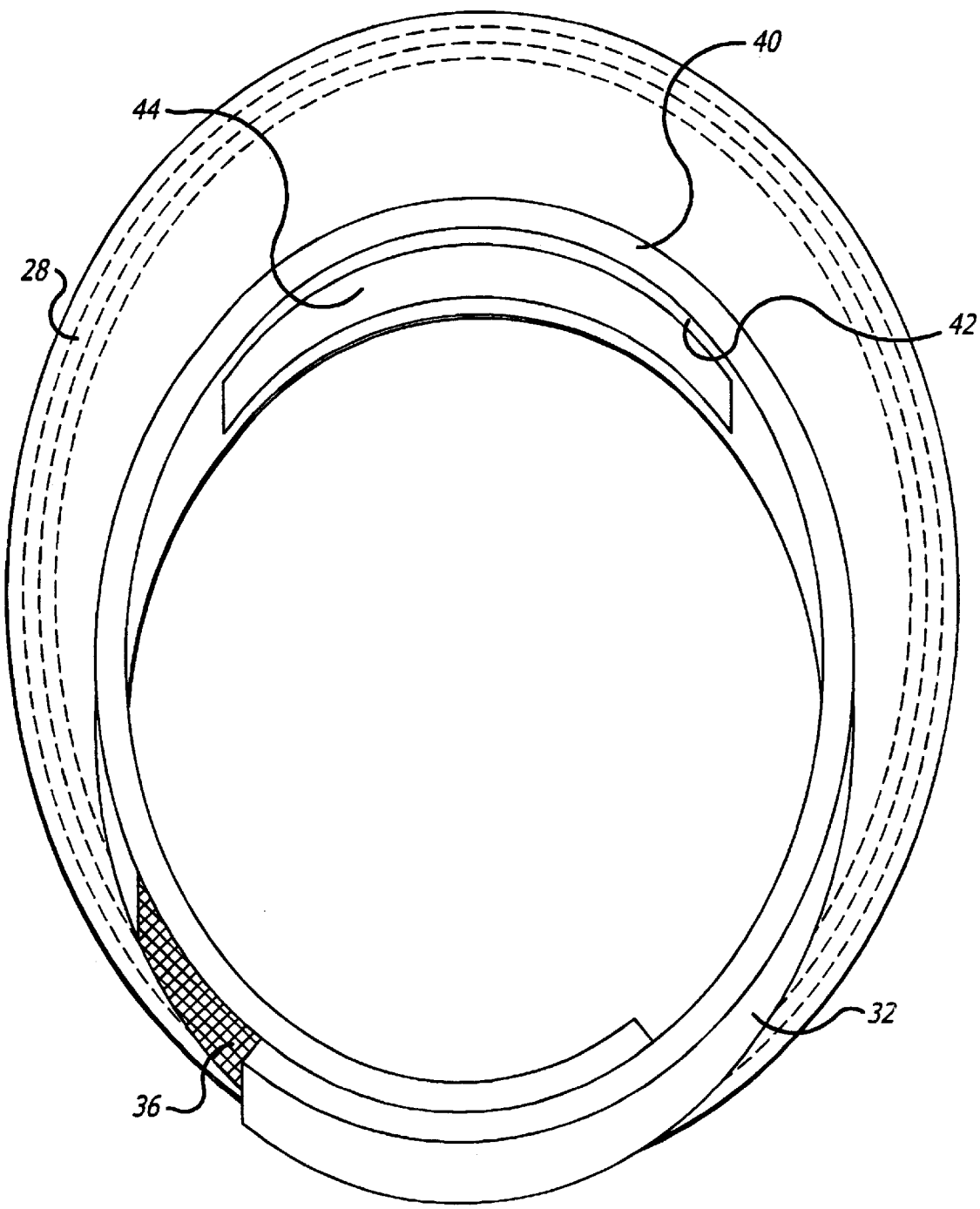
FIG. 4 is a rear perspective view of the auxiliary visor of the invention.

FIG. 4 is a rear perspective view of the auxiliary visor 10 of the invention. As can be seen in this view, a strip 42 of material is joined to the back panel. Such strip 42 comprises fabric having a central band 44 of frictional non-stick material for providing and maintaining secure gripping between the outer surface of a riding helmet and the auxiliary visor 10. The inventor has found that a composition consisting of 46 per cent polyester, 29 percent LATEX based rubber and 25 per cent silicone provides the degree of non-stick adhesion and reusability required to assure that the wearer needn't be concerned with the possibility of the visor unintentionally dislodging during normal use.

Thus it is seen that the present invention provides an auxiliary visor for a riding helmet. By employing the teachings of the invention, one is provided with a device that is compatible with and fits all riding helmet sizes, secure in use and shades the wearer's entire face (as well as neck and a portion of the shoulders) without impeding vision.

While this invention has been disclosed with reference to its presently-preferred embodiment, it is not limited thereto. Rather, this invention is only limited insofar as it is defined by the following set of patent claims and includes within its scope all equivalents thereof.

What is claimed is:

1. An auxiliary visor adaptable to a riding helmet comprising, in combination:

a) a bill for shading a wearer having at least one edge;

b) a band fixed to said at least one edge of said bill;

c) said band comprising an elongated member of flexible material having interior and exterior surfaces and having opposed ends;

d) a fastener for securing said band to surround and apply an inwardly-directed force to the exterior surface of a helmet, said fastener comprising mating cooperative elements fixed in facing relationship to said opposed ends of said member; and e) said interior surface comprising a strip of frictional material of predetermined non-sticky composition for imposing, in combination with said inwardly-directed force, a frictional force for retaining said band to a riding helmet.

2. A visor as defined in claim 1 wherein said bill is arranged to overlie and extend beyond the bill of a riding helmet.

3. A visor as defined in claim 1 wherein each of said mating cooperative elements comprises VELCRO.

4. A visor as defined in claim 1 wherein said flexible material is arranged substantially parallel to said strip of material.

5. A visor as defined in claim 4 wherein:

a) said strip is of permeable fabric; and b) said frictional material impregnates said fabric interior to said strip.

* * * * *